(12) United States Patent
Liu

(10) Patent No.: US 8,198,343 B2
(45) Date of Patent: Jun. 12, 2012

(54) SELF-ADHESIVE DENTAL CEMENT

(75) Inventor: Huaibing Liu, Dover, DE (US)

(73) Assignee: DENTSPLY International Inc., York, PA (US)

( * ) Notice: Subject to any disclaimer, the term of this patent is extended or adjusted under 35 U.S.C. 154(b) by 70 days.

(21) Appl. No.: 12/150,254

(22) Filed: Apr. 25, 2008

(65) Prior Publication Data

US 2009/0048364 A1 Feb. 19, 2009

Related U.S. Application Data

(60) Provisional application No. 60/926,134, filed on Apr. 25, 2007.

(51) Int. Cl.
*A61K 6/08* (2006.01)
*A61K 6/083* (2006.01)
*C08F 2/50* (2006.01)

(52) U.S. Cl. ........... 522/24; 522/27; 522/83; 522/103; 522/171; 522/182; 523/116

(58) Field of Classification Search ............... 522/17, 522/27, 103, 83, 24, 182, 171; 523/116
See application file for complete search history.

(56) References Cited

U.S. PATENT DOCUMENTS

| | | | |
|---|---|---|---|
| 3,991,008 A * | 11/1976 | Temin et al. | 523/115 |
| 4,596,857 A * | 6/1986 | Doi et al. | 525/255 |
| 4,816,495 A | 3/1989 | Blackwell et al. | |
| 4,966,934 A | 10/1990 | Huang et al. | |
| 5,063,257 A | 11/1991 | Akahane et al. | |
| 5,154,762 A | 10/1992 | Mitra et al. | |
| 5,639,808 A | 6/1997 | Coggio et al. | |
| 6,127,451 A | 10/2000 | Qian | |
| 6,191,190 B1 | 2/2001 | Blackwell et al. | |
| 6,214,101 B1 | 4/2001 | Nakaseko | |
| 6,391,940 B1 | 5/2002 | Blackwell et al. | |
| 6,500,004 B2 | 12/2002 | Jensen et al. | |
| 6,818,682 B2 | 11/2004 | Falsafi et al. | |
| 6,844,080 B2 | 1/2005 | Kneafsey et al. | |
| 7,166,651 B2 | 1/2007 | Qian | |
| 7,214,726 B2 | 5/2007 | Qian | |
| 7,275,932 B2 | 10/2007 | Jin et al. | |
| 2004/0235981 A1 | 11/2004 | Qian | |
| 2005/0014861 A1 | 1/2005 | Qian | |

FOREIGN PATENT DOCUMENTS

| EP | 1479364 | 11/2004 |
|---|---|---|
| EP | 1502569 | 2/2005 |

* cited by examiner

*Primary Examiner* — Susan W Berman

(74) *Attorney, Agent, or Firm* — Leana Levin; Douglas J. Hura; David A. Zdurne

(57) ABSTRACT

A dental, paste/paste self-adhesive cement includes a polymerizable acidic monomer or monomer mixtures; a polymerizable non-acidic monomer or monomer mixtures, a photo-initiator and/or a co-initiator, a reducing agent such as a benzoylthiourea and other substituted benzoylthiourea, an oxidizing agent, a thermal stabilizer and a glass filler.

6 Claims, No Drawings

SELF-ADHESIVE DENTAL CEMENT

TECHNICAL FIELD

The present invention generally relates to dental cements. More particularly, the invention relates to dental cements that are self-adhesive. The cement is preferably dual curing.

BACKGROUND

A variety of cements have been used in dentistry as restorative filling materials and to retain restorations or appliances in a fixed position within the mouth. The common commercially available dental cements include zinc phosphate, polycarboxylate, glass ionomer, resin modified glass ionomer, compomer and resin composite. The ability of the glass ionomer, resin modified glass ionomer and compomer to release fluoride and to bond chemically to tooth structure has resulted in their uses as bases for cementation. The main drawbacks of the cements in this category are its well-documented susceptibility to moisture attack and subsequent solubility if exposed to water during the initial setting period. In addition, excessive water sorption and swelling may cause tooth and ceramic fracture and thus their application are normally limited to non-ceramic indirect restorations. Resin cements are used for retention of orthodontic brackets, all-ceramic veneers, crowns and inlays, and resin-bonded bridges because of their strength and ability to bond to acid-etched enamel and dentin treated with a dentin bonding agent.

Resin cements are variations of filled BIS-GMA resin and other methacrylates. They polymerize through chemically initiated mechanisms, photopolymerization, or a combination of both. Adhesion to enamel occurs through the micromechanical interlocking of resin to the hydroxyapatite crystals and rods of etched enamel. Adhesion to dentin requires multiple steps, beginning with the application of an acid, or dentin conditioner to remove the smear layer, smear plugs, open and widen tubules, and demineralize the top 2 to 5 µm of dentin, followed by the application of a hydrophilic primer and a bonding agent or a single-bottle bonding agent and a self-cure activator. The complexity and technique sensitivity have hindered the popularity of the resin cements.

A resin cement which combines the use of adhesive and cement in one single application, eliminating the need for pre-treatment of both tooth and restoration, would be advantageous. It would be even more advantageous that the potential cement is kept in a convenient two-part past/paste delivery system. However, it is a great challenge to combine the essential ingredients fulfilling the functions of etching, priming and bonding. Self-curing capability is the minimum requirement for a cement because for most indirect restorations it is difficult for light to access the cement with sufficient intensity to achieve adequate light-cure. A commonly used self-cure initiating system is benzoyl peroxide/aromatic tertiary amine. In order to render self-etching and self-adhesive capability to the cement, an acidic monomer has to be included in the formulation. Thus, the acid-base reaction converting tertiary amine to the protonated form effectively deactivates the initiating system. The degree of polymerization decreases or even no polymerization occurs. The other problem with the initiating system of benzoyl peroxide/aromatic amine is storage instability of benzoyl peroxide, particularly in the presence of any acidic species. Therefore, a self-cure initiating system comprising of non-amine reducing agent and a thermally stable oxidizing agent would be highly desirable.

European Patent Application EP 1479364A1 and US Patent Application UA20040235981 disclose a dental composition which etches, primes, and cements in one step and is shelf stable. The composition can be used as a restorative dental composition, an endodontic composition, and an orthodontic composition, and has the following components:

(a) at least one acidic compound containing at least one acidic moiety selected from the group consisting of

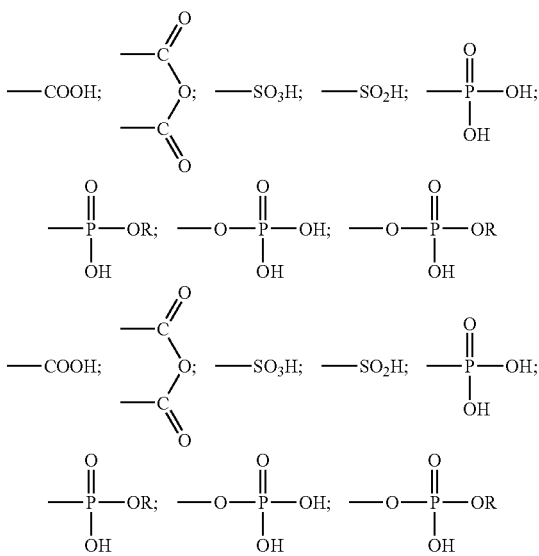

where R is an alkyl or aryl group;

(b) at least one polymerizable monomer without any acidic group where the polymerizable group is selected from the group consisting of an acrylate, a methacrylate, and a vinyl group;

(c) a substituted thiourea selected from the group consisting of 1-(2-pyridyl)-2-thiourea and 1-(2-tetrahydrofurfuryl)-2-thiourea; and (d) a hydroperoxide compound with at least one hydroperoxide group attached to a tertiary carbon.

European Patent Application EP1502569A1 and US Patent Application UA20050014861 disclose a method for providing and using a two-part paste-paste self-adhering dental composition which allows combined etching and priming of a dental surface. The method provides a paste/paste two-part self-adhering dental composition comprising (a) at least one acidic compound containing at least one acidic moiety selected from the group consisting of

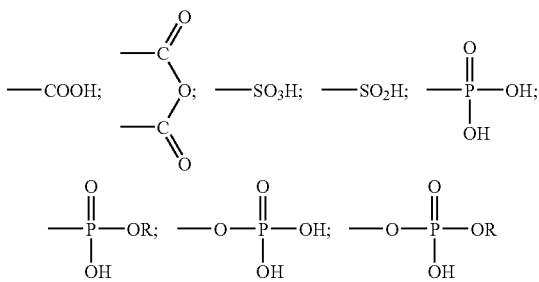

where R is an alkyl or aryl group;

(b) at least one polymerizable monomer without any acidic group where the polymerizable group is selected from the group consisting of an acrylate, a methacrylate and a vinyl group;
(c) at least one finely divided filler;
(d) at least one reducing agent; and
(e) at least one oxidizing agent;

And providing instructions for mixing the two pastes where the ratio of a first paste containing (a) or a higher concentration of (a) to a second paste not containing (a) or containing a lower concentration of (a) is greater than 1:1 (by volume).

An amount of an acidic monomer is essential for self-etch and self-adhesive capability of SACs. Problems associated with the need of an acidic monomer in the formulation:

Premature gelling of resin pastes due to the acid-catalyzed decomposition of benzoyl peroxide, a commonly used oxidizer for dental redox initiator.

Deactivation of self-cure initiating system because of the acid-base reaction converting a tertiary amine, a commonly used reductant for dental redox initiator, to its protonated form.

The acidic functional group of an acidic monomer is hydrophilic and the possible excessive water sorption and swelling may cause tooth and ceramic fracture.

SUMMARY OF THE INVENTION

It is desired to provide a self-adhesive cement (SAC) that can be packaged in two-part paste/paste dual-barrel syringes and mixed (1:1 volume) prior to application readily through automix tips. The material should be useful for adhesive cementation of indirect metal, PFM, reinforced ceramic and composite restorations (including unit crowns and bridges); non-reinforced ceramic anterior and bicuspid restorations (including unit crowns and bridges); non-reinforced or reinforced ceramic, and composite inlays/onlays; posts; or any other such dental uses in the oral cavity. The use of any etchant and bonding agent on tooth surface should be unnecessary because the SAC alone should produce a sufficient bond between the restoration and tooth structure. Its bond strength and mechanical properties are at least comparable to or better than known adhesive materials. It should have storage stability with shelf-life at room temperature at least about 18 months and Its color should not change perceivably over time in an oral environment.

According to the invention, an acidic monomer with four polymerizable functional group is employed. Cumene hydroperoxide, a thermally stable and acid-tolerant hydroperoxide acts as the oxidizer for the redox initiator and is included in the paste together with the acidic monomer. Benzoyl thiourea acts as the reductant for the redox initiator and is included in the paste without any acidic monomer. Benzoyl thiourea/cumene hydroperoxide as self-cure initiating system is not adversely affected by any acidic monomers. On the contrary, the initiating efficiency of benzoyl thiourea/cumene hydroperoxide is enhanced by the presence of acidic monomers. The cure kinetics can be conveniently controlled with the type and the concentration of acidic monomer.

In general, according to the present invention, a paste/paste self-adhesive cement, shelf-stable for at least about 18 months, comprises
(i) 1 to 50% by weight of polymerizable acidic monomer or monomer mixtures;
(ii) 1 to 50% polymerizable non-acidic monomer or monomer mixtures;
(iii) 0.01 to 1% photoinitiator
(iv) 0.01 to 1% photo co-initiator
(v) 0.1 to 2% reducing agent selected from benzoylthiourea and other substituted benzoylthiourea
(vi) 0.1 to 2% oxidizing agent
(vii) 0.01 to 0.1% thermal stabilizer
(viii) about 25% to 75% glass filler

PREFERRED EMBODIMENTS FOR CARRYING OUT THE INVENTION

The paste/paste self-adhesive resin cement of the present SAC (self-adhesive cement) invention, is preferably dual-curing and can be delivered in double-barrel syringes or the like. It is designed for adhesive cementation of indirect metal, PFM, reinforced ceramic and composite restorations (including unit crowns and bridges); non-reinforced ceramic anterior and bicuspid restorations (including unit crowns and bridges); non-reinforced or reinforced ceramic and composite inlays/onlays; posts; or any other cementation that may be required in the oral cavity. Although it may be used if desired, the use of any etchant and bonding agent on the tooth surface is unnecessary because the present SAC invention alone produces a sufficient bond between the restoration and tooth structure.

1. Self-adhesive cement is packaged in two-part paste/paste dual-barrel syringes and mixed (preferably in a 1:1 volume) prior to application readily through standard automix tips.
2. It is used for cementation of indirect restorations without pre-treatment of dentin or enamel.
3. Its bond strength and mechanical properties are at least comparable to or better than the leading competitive materials.

Principle Self-adhesive Compomer Cement and Calibra Esthetic Resin Cement are two related cement products on the market (available from DENTSPLY International of York, Pa.) with the overlapping indications. Principle is a powder/liquid system and has to be proportioned and hand mixed, which is inconvenient to dental practitioners and may cause inconsistency in handling and performance. Calibra has no inherent adhesion to tooth structure and thus relies on separate etching and bonding steps. Moreover, Calibra base and catalyst are packaged in separate syringes and has to be proportioned and hand-mixed. The new SAC is also easily differentiated from the commercial competitive self-adhesion resin cement product RelyX Unicem (available from 3M Espe, St. Paul, Minn.) which is an encapsulated power-liquid system and needs to be mixed with extra, space-consuming equipment. The unique chemistry and judicious selection of ingredients in the present SAC invention render the formulation deliverable from automix syringe, storage and color stable, dimensionally stabile, and most importantly, allows bonding to tooth structure without extra steps or bonding agents.

To have self-etching and self-adhesive capability, an acidic monomer of PENTA (dipentaerythritol pentaacrylate monophosphate) is included. As discussed before, the commonly used self-cure initiating system benzoyl peroxide/aromatic tertiary amine does not function in such moderately acidic condition. Therefore, an acid-tolerant self-cure initiating system is prerequisite for a potential self-adhesive cement. It is even more challenging to have a shelf-stable paste/paste packaging instead of a powder/liquid system. Most redox initiating systems are not stable and prematurely decompose or polymerize (gel) the resins if allowed to be solubilized.

A novel self-cure initiating system which functions under moderately or strong acidic condition was identified for the present SAC invention. Benzoyl thiourea as the reducing agent is contained in the base paste. Cumene hydroperoxide is thermally stable and rather resistant against acid-induced degradation normally seen with benzoyl peroxide. Thus, cumene hydroperoxide as the oxidizer is included in the catalyst paste together with the acidic monomer and other dimethacrylates. On mixing the base/catalyst pastes, benzoyl thiourea and cumene hydroperoxide act as a redox pair and generate initiating radicals, resulting in polymerization of monomers and formation crosslinked networks. It is important to note that benzoyl thiourea/cumene hydroperoxide as self-cure initiating system is not adversely affected by any acidic monomers. On the contrary, the initiating efficiency of benzoyl thiourea/cumene hydroperoxide is enhanced by the presence of acidic monomers. The new initiating system developed in this project is distinguished from those disclosed in European Patent Application EP1479364A1 and US Patent Application UA20040235981. The former consists of benzyol thiourea as the reducing agent while the latter was a substituted thiourea selected from the group consisting of 1-(2-pyridyl)-2-thiourea and 1-(2-tetrahydrofurfuryl)-2-thiourea.

The method of providing two-part self-adhesive cement in the potential product derived from this project is clearly different from those disclosed in European Patent Application EP1502569A1 and US Patent Application UA20050014861. The present SAC invention is packaged in two-part paste/paste dual-barrel syringes and mixed (1:1 volume) prior to application through auto mix tips. The self-adhesive cement described in the above patent applications is at the ratio of catalyst to base greater than 1:1 (by volume).

TABLE 1 provides a listing and preferred and useful ranges of composition components.

TABLE 1

| Component | Chemical Name | CAS # | Base Formulation Ranges | Base Preferred % Weight | Catalyst Formulation Ranges | Catalyst Preferred % Weight |
|---|---|---|---|---|---|---|
| UDMA | 2-Methyl-acrylic acid 1-methyl-2-{3,5,5-trimethyl-6-[1-methyl-2-(2-methyl-acryloyloxy)-ethoxycarbonyl amino]-hexylcarbamoyloxy}-ethyl ester | 105883-40-7 | 3-15 | 7.65 | 3-15 | 6.76 |
| EDPADMA Urethane | Reaction product of Bis-GMA with Hexamethylene Diisocyanate (HMDI) in EBPADMA | 41637-38-1 | 3-15 | 7.65 | 3-15 | 6.76 |
| TEGDMA | 2-Methyl-acrylic acid 2-{2-[2-(2-methyl-acryloyloxy)-ethoxy]-ethoxy}-ethyl ester | 109-16-0 | 3-15 | 5.56 | 3-15 | 4.92 |
| TMPTMA | 2-Methyl-acrylic acid 2,2-bis-(2-methyl-acryloyloxymethyl)-butyl ester | 3290-92-4 | 3-15 | 6.96 | 3-15 | 6.15 |
| PENTA | 2-Methyl-acrylic acid 3-(2-methyl-acryloyloxy)-2-(2-methyl-acryloyloxymethyl)-2-[3-(2-methyl-acryloyloxy)-2-(2-methyl-acryloyloxymethyl)-2-phosphonooxymethyl-propoxymethyl]-propyl ester | 87699-25-0 | 0 | 0 | 3-15 | 8.08 |
| CHPO | 2-Isopropyl-phenyl-hydroperoxide | 80-15-9 | 0 | 0 | 0.1-5.0 | 0.97 |
| BTU | Benzoylthiourea | 614-23-3 | 0.1-1 | 0.63 | 0 | 0 |
| DMABN | 4-Dimethylamino-benzonitrile | 1197-19-9 | 0.02-0.2 | 0.080 | 0 | 0 |
| CQ | 1,7,7-Trimethyl-bicyclo[2.2.1]heptane-2,3-dione | 10373-78-1 | 0.02-0.2 | 0.064 | 0 | 0 |
| L-TPO | (Diphenyl-phosphinoyl)-(2,4,6-trimethyl-phenyl)-methanone | 75980-60-8 | 0.02-0.2 | 0.098 | 0 | 0 |
| BHT | Phenol, 2,6-bis (1,1-dimethylethyl-4-methyl) | 128-37-0 | 0.005-0.004 | 0.018 | 0.005-0.2 | 0.04 |
| Unival M40 | 2-Hydroxy-4-Methoxybenzophenone | 131-57-7 | 0.1-1 | 0.29 | 0.1-1 | 0.34 |
| Silanated EG 9726 Glass I | γ-Methacryloxypropyltrimethoxysilane surface treated barium fluoroalumino borosilicate glass | 2530-85-0 65997-18-4 | 25-75 | 49.77 | 25-75 | 47.50 |
| Silanated EG 9726 Glass II | γ-Methacryloxypropyltrimethoxysilane surface treated barium fluoroalumino borosilicate glass | 2530-85-0 65997-18-4 | 5-35 | 16.54 | 5-35 | 15.77 |
| Cab-O-Sil TS-720 | Fumed Silica (SiO$_2$) | 67762-90-7 68611-44-9 | 0.1-2 | 0.78 | 0.1-2 | 0.73 |
| Aerosil R972 | | 67762-90-7 68611-44-9 | 0.5-5.0 | 2.13 | 0.5-5.0 | 1.98 |
| Calcium Hydroxide | Calcium Hydroxide | 1302-62-0 | 0-5.0 | 1.78 | 0-5.0 | 0 |
| TiO$_2$ #3328 | Titanium Dioxide | 13463-67-7 | 0 | 0 | 0 | 0 |
| Iron Oxide Pigments | Iron Oxide, Pigments | 1332-37-2 51274-00-1 | 0 | 0 | 0 | 0 |

TABLE 1-continued

| | | | Base | | Catalyst | |
|---|---|---|---|---|---|---|
| Component | Chemical Name | CAS # | Formulation Ranges | Preferred % Weight | Formulation Ranges | Preferred % Weight |
| | | 1317-61-9 | | | | |
| TOTAL | | | | 100 | | 100.00 |

General Experimental

The following components are used herein:

2,2-Bis[4-(2-hydroxy-3-methacryloylpropoxy)-phenyl)]-propane (Bis-GMA): polymerizable matrix resin Ethoxylated bisphenol A dimethacrylate (EBPADMA): polymerizable matrix resin Triethyleneglycoldimethacrylate (TEGMA): Reactive diluent Trimethylolpropane Trimethacrylate (TMPTMA): Reactive diluent Dipentaerythritol pentaacrylate phosphoric acid ester (PENTA): Acidic monomer, adhesion promoter, Camphorquinone (CQ): photoinitiator 4-Dimethylamino-benzonitrile (DMABN): photo co-initiator Ethyl-4-(N,N,-dimethylamino) benzoate (EDAB): photo co-initiator Diphenyl(2,4,6-trimethylbenzoyl)-phosphine oxide (L-TPO): photoinitiator Cumene hydroperoxide (CHP): self-cure initiator Benzoylthiourea (BTU): self-cure co-initiator Barium boron fluoro aluminosilicate glass (BaBFAlSi glass): filler Strontium calcium aluminosilicate glass (SrCaAlSi glass): filler Testing Shear Bond Strength of Paste/Paste Self-adhesive Cement to Human Tooth Substrates (Dentin or Enamel):

Extracted human molars were immersed in water and stored in a 4° C. refrigerator prior to use. Dentin or enamel was sanded using wet 320 grit abrasive paper and then 600 grit. The surface was blot-dried with Kimwipes. Cut plastic straws (3.65 mm in diameter) were filled with the mixed cement and positioned onto the dentin or enamel surface. The flash was gently removed using a dental explorer and the cement was left to self-cure or light with Spectrum 800 at 550 mw/cm$^2$. The samples were embedded in tray resin and the posts were ensured to be perpendicular to the bonding surface.

The shear bond strength was obtained in compressive shear mode with a Instron at a crosshead speed of 1 mm/min.

EXAMPLE 1

Base Paste
10.93% by weight of Bis-GMA,
12.75% by weight of EBPADMA,
10.93% by weight of TEGDMA,
1.82% by weight of TMPTMA,
0.02% by weight of BHT,
0.38% by weight of BTU,
0.11% by weight of CQ,
0.30% by weight of EDAB,
0.76% by weight of L-TPO,
61.23% by weight of silianated barium boron fluoro aluminosilicate glass,
0.77% by weight of Cab-O—Sil TS 720

Catalyst Paste:
7.30% by weight of Bis-GMA,
8.30% by weight of EBPADMA,
8.10% by weight of TEGDMA,
1.82% by weight of TMPTMA,
11.00% by weight of PENTA,
0.02% by weight of BHT,
1.46% by weight of CHP,
61.23% by weight of silianated barium boron fluoro aluminosilicate glass,
0.77% by weight of Cab-O—Sil TS 720

When the base paste was mixed with the catalyst paste (1:1 by volume), the shear bond strength of the cement in self-cure mode was 3.6 MPa on dentin without prior chemical treatment of the tooth. The baseline set time of the mixed cement was 3 minutes and 45 seconds. After aging at 45° C. for 12 weeks, the set time was 4 minutes and 30 seconds, no significant change from the baseline. The baseline diametral tensile strength of the cement in self-cure mode was 36.1 MPa. After aging at 45° C. for 12 weeks, the strength was retained at 38.2 Mpa.

EXAMPLE 2

Base Paste
11.19% by weight of Bis-GMA,
13.06% by weight of EBPADMA,
11.19% by weight of TEGDMA,
1.87% by weight of TMPTMA,
0.02% by weight of BHT,
0.38% by weight of BTU,
0.08% by weight of CQ,
0.15% by weight of DMABN,
0.08% by weight of L-TPO,
61.18% by weight of strontium calcium aluminosilicate glass,
0.80% by weight of Cab-O—Sil TS 720

Catalyst paste: same as the one illustrated in Example 1.

When the base paste was mixed with the catalyst paste (1:1 by volume), the shear bond strength of the cement in self-cure mode was 3.7 MPa on dentin without prior chemical treatment of the tooth. The baseline set time of the mixed cement was 5 minutes. After aging at 45° C. for 9 weeks, the set time was 5 minutes and 50 seconds, no significant change from the baseline. The diametral tensile strength of the cement in self-cure mode was 34.7 MPa.

EXAMPLE 3

Base Paste
8.72% by weight of Bis-GMA,
10.18% by weight of EBPADMA,
8.72% by weight of TEGDMA,
1.46% by weight of TMPTMA,
0.01% by weight of BHT,
0.07% by weight of CQ, 0.08% by weight of DMABN,
0.10% by weight of L-TPO,
67.38% by weight of strontium calcium aluminosilicate glass,
0.88% by weight of Cab-O—Sil TS 720
1.75% by weight of calcium hydroxide
Catalyst Paste:
7.97% by weight of Bis-GMA,
9.30% by weight of EBPADMA,
7.98% by weight of TEGDMA,
1.33% by weight of TMPTMA,
8.55% by weight of PENTA,
0.01% by weight of BHT,
0.86% by weight of CHP,
63.2% by weight of silianated barium boron fluoro aluminosilicate glass,
0.80% by weight of Cab-O—Sil TS 720

When the base paste was mixed with the catalyst paste (1:1 by volume), the work time was 2 minutes and 45 seconds and set time of the mixed cement was 4 minutes. The shear bond strength of the cement in self-cure mode was 5.0 MPa on dentin and 11.2 MPa on enamel without prior chemical treatment of the tooth. The shear bond strength of the cement in light-cure mode was 5.1 MPa on dentin and 17.7 MPa on enamel without prior chemical treatment of the tooth. In self-cure mode, the compressive strength, diametral tensile strength and flexural strength of the cement were 289 MPa, 38 MPa and 68 Mpa, respectively while in light-cure mode they were 296 MPa, 43 MPa and 90 MPa, respectively.

What is claimed is:

1. A self-adhesive dental cement comprising two pastes,
wherein a first paste includes from 1 to 50% by weight of at least one polymerizable acidic monomer and 0.1 to 5% by weight of cumene hydroperoxide oxidant;
wherein a second paste includes from 1 to 50% by weight of at least one polymerizable non-acidic monomer and from 0.1 to 2% by weight of a benzoylthiourea reducing agent,
wherein the first paste and the second paste are present in a 1:1 by volume ratio,
wherein the first paste comprises Bis-GMA, EBPADMA, TEGDMA, TMPTMA, Dipentaerythritol pentaacrylate phosphoric acid ester (PENTA), BHT, Cumene hydroperoxide (CHP) and a filler material, and
wherein the second paste comprises 2.2-Bis[4-(2-hydroxy-3-methacryloylpropoxy)-phenyl)]-propane (Bis-GMA), Ethoxylated bisphenol A dimethacrylate (EBPADMA), 2-Methyl-acrylic acid 2-{2-[2-(2-methyl-acryloyloxy)-ethoxy]-ethoxy}-ethyl ester (TEGDMA), 2-Methyl-acrylic acid 2.2-bis-(2-methyl-acryloyloxymethyl)-butyl ester (TMPTMA), Phenol, 2,6-bis (1,1-dimethylethyl-4-methyl) (BHT), Benzoylthiourea (BTU), 1,7,7-Trimethyl-bicyclo[2.2.1]heptane-2,3-dione (CQ), Ethyl-4-(N,N,-dimethylamino) benzoate (EDAB), (Diphenyl-phosphinoyl)-(2,4.6-trimethyl-phenyl)-methanone (L-TPO), and a filler material.

2. A dental cement as in claim 1, at least one of the first paste and the second paste further comprise from about 0.01 to about 1% by weight of a photoinitiator.

3. A dental cement as in claim 2, at least one of the first paste and the second paste further comprise from about 0.01 to about 1% by weight of a photo co-initiator.

4. A dental cement as in claim 3, further comprising an additive selected from the group consisting of an oxidizing agent, a thermal stabilizer and a filler material.

5. A self-adhesive dental cement comprising two pastes,
wherein a first paste includes from 1 to 50% by weight of at least one polymerizable acidic monomer and 0.1 to 5% by weight of cumene hydroperoxide oxidant;
wherein a second paste includes from 1 to 50% by weight of at least one polymerizable non-acidic monomer and from 0.1 to 2% by weight of a benzoylthiourea reducing agent,
wherein the first paste and the second paste are present in a 1:1 by volume ratio, and
wherein the at least one polymerizable acidic monomer of the first paste is an acidic monomer with at least four polymerizable functional groups and the at least one polymerizable non-acidic monomer is a (meth)acrylate.

6. A dental cement as in claim 5, where the acidic monomer has five polymerizable functional groups.

* * * * *